United States Patent [19]

Cheesman

[11] 4,081,533

[45] Mar. 28, 1978

[54] METHOD OF REDUCING MAMMALIAN FERTILITY AND DRUGS THEREFOR

[75] Inventor: Dean W. Cheesman, Kentfield, Calif.

[73] Assignee: Regents of the University of California, Berkeley, Calif.

[21] Appl. No.: 719,659

[22] Filed: Sep. 1, 1976

[51] Int. Cl.$^2$ .................... A61K 37/00; C07C 103/52
[52] U.S. Cl. ........................... 424/177; 260/112.5 LH
[58] Field of Search ............... 424/177; 260/112.5 LH

[56] References Cited

U.S. PATENT DOCUMENTS 3,883,498  5/1975  Gillessen et al. .................... 424/177
3,915,947  10/1975  Shields .................... 424/177

Primary Examiner—Delbert R. Phillips
Attorney, Agent, or Firm—Phillips, Moore, Weissenberger, Lempio & Majestic

[57] ABSTRACT

The pre-ovulatory surge of luteinizing hormone from the pituitary gland is selectively suppressed or eliminated by introducing nonapeptide, 8-arginine vasotocin, or the tripeptide, propyl-arginyl-glycinamide, into the subject. Analogs and related peptides also exhibit a similar inhibitory effect. This anovulatory effect in the female, or reduction in spermatogenesis in the male, results in loss of fertility.

17 Claims, No Drawings

METHOD OF REDUCING MAMMALIAN FERTILITY AND DRUGS THEREFOR

BACKGROUND OF THE INVENTION

Mammalian female fertility involves a cyclic phenomenon regulated by an interplay of protein hormones (gonadotropins - luteininizing hormone (LH) follicle stimulating hormone (FHS), and prolactin), from the pituitary, and steroid hormones (estrogens and progesterone) from the ovary. The gonadotropins act in a positive manner to stimulate production of the steroids. In turn, the gonadal steroids exert control over pituitary secretion of gonadotropins, resulting in a repeating, fairly predictable release of gonadotropins and steroids, each regulating the other.

The gonodotropins, acting on the ovary via the circulatory system, are directly responsible for follicular growth and maturation and release of the ovum from the ovarian follicle. The steroids maintain the reproductive tract and provide environments suitable for fertilization in the oviduct and implantation and maintenance of the embryo in the uterus.

Once each cycle, when the ovum inside the ovarian follicle is mature, changing blood levels of steroids inform the brain, causing the release of a large amount of LH. This pre-ovulatory surge of LH initiates ovulation with release of the ovum into the oviducts, where contact with sperm results in a fertilized ovum. The ovum then passes into the uterus, implants in the uterine wall and pregnancy has occured. Selective suppression of the pre-ovulatory surge of LH results in loss of ovulation and subsequent loss of fertility since the mature ovum is not made available to the sperm.

In the case of the male, the analogous FSH is responsible for spermatogenesis while LH is responsible for production of androgens which act to regulate pituitary secretion of gonadotropins. The androgens also promote spermatogenesis, matures sperm cells, and maintain the male reproductive tract. Therefore, any interference with pituitary secretion of gonadotropins will decrease or eliminate sperm production.

To date, the majority of birth control drugs depend on the introduction of continued physiological high levels of estrogen and/or progesterone into the subject. These steroids inhibit pituitary secretion of gonadotropins with resultant loss of cyclic activity and a relatively quiescent ovary which does not produce mature ovum. Well documented side effects of present steroid birth control drugs result from the continuous high levels of steroids and the fact that steroids act throughout the body, mediating various processes. Side effects include carcinogenic properties, increased blood pressure high incidence of blood clots, etc. An endogenously occurring peptide birth control drug would, (1) not involve introducing high steroid blood levels, thus eliminating the above side effects, (2) act on the gonadotropin hormones which act only on the ovary, and indirectly cause a decrease rather than an increase of endogenous steroids, (3) involve the introduction of a naturally occurring compound, for which the body possesses the necessary metabolic pathways, and (4) stop the process of reproduction prior to fertilization, thus eliminating a religious objection to the termination of life conception.

BRIEF DESCRIPTION OF THE INVENTION

This invention relates to a method for reducing or eliminating the fertility of mammalian organisms by treatment with peptide compositions that selectively suppress the pre-ovulatory surge of luteinizing hormone (LH) from the pituitary and subsequently reduce or eliminate ovulation, in the case of the female, or spermatogenesis, in the case of the male.

Gonadotropin secretion from the anterior pituitary gland is under the direct influence of fairly specific polypeptide factors in the hypothalmic area of the brain. A complex regulatory system, which includes the nervous system and ovarian steroids in the blood, governs sending these hypothalamic, polypeptide releasing and inibiting factors to the anterior pituitary via a closed portal system, and causing secretion, or inhibition of secretion. A birth control drug selectively influencing the hypothalamic inhibiting and releasing factors is obviously much more subtle than introducing large amounts of steroids into the subject. It has now been determined that a specific group of peptides, at least one of which occurs naturally in the mammalian organism, selectively suppresses the preovulatory LH surge and subsequent release of ova.

In particular, these peptides are the nonapeptide, 8-arginine vasotocin, which occurrs as a natural component of mammalian pineal secretions, and analogues thereof; and the tripeptide, prolyl-arginyl-glycinamide, and analogues thereof.

When pharmacologically acceptable formulations of the nonapeptides or tripeptides are administered into the mammalian organism during pre-ovulation, the characteristic LH surge from the pituitary is suppressed, resulting in greatly diminished, or even complete absence of ovulation.

The peptide effect is transitory and further quantities must be introduced into the subject at the onset of the next ovulation, otherwise the characteristic LH surge will occur and ovulation will take place in the normal manner.

It is another object of the invention to suppress fertility by interfering with the pre-ovulation surge of luteinizing hormone from the pituitary gland.

It is another object of the invention to provide a nonapeptide, 8-arginine vasotocin, or the tripeptide, prolyl-arginyl-glycinamide, as pharmacological materials in the suppression of mammalian fertility.

It is yet another object of the invention to introduce 8-arginine vasotocin or prolyl-arginyl-glycinamide, into the mammalian female subject in amounts sufficient to suppress the luteinizing hormone surge from the pituitary gland prior to ovulation.

It is still another object of the invention to introduce 8-arginine vasotocin, or prolyl-arginyl-glycinamide, into a male mammalian subject to suppress spermatogenesis.

Other objects and advantages of the invention will become apparent from a review of the following description and the claims appended hereto.

DETAILED DESCRIPTION OF THE INVENTION

The nonapeptide 8-arginine vasotocin occurs in the pineal secretions and its presence and structure were disclosed by the present inventor in several articles published in 1970. The article "Isolation and Characterization of a Gonadotropin-Inhibiting Substance from the Bovine Pineal Gland" was published in the Proceedings of the Society for Experimental Biological Medicine, 1970, Vol. 133, pg. 1254; while the article "Structural Elucidation of a Gonodotropic-Inhibiting Substance from the Bovine Pineal Gland" was published in Biochimica Biophysica Acta, 1970, Vol. 207, pgs. 247-253.

In the above noted publications it was reported that a gonadotropin inhibiting substance, 8-arginine vasotocin occurs in the bovine pineal gland. The 8-arginine vasotocin was shown to be a cyclic nonapeptide having the following structure:

Cys-Tyr-Ileu-Glu (NH$_2$)-Asp(NH$_2$)-Cys-Pro-Arg-Gly(NH$_2$)

wherein the abbreviated notations for the amino acids are understood as follows: Cys = cysteine, Tyr = tyrosine, Ileu = isoleucine, Glu = glutamic acid, Asp = aspartic acid, Pro = Proline, Arg = arginine, and Gly = glycine. It is to be further understood that the notations, Glu(NH$_2$) Gly(NH$_2$) and, Asp (NH$_2$) refer to glutamine, glycine amide and asparagine, respectively.

8-arginine vasotocin, as indicated by the linkage between the two cysteine groups has a cyclic structure with a disulfide bridge linking the sulfur atoms occuring on the two cysteine functional groupings.

It has now been determined that when 8-arginine vasotocin is administered to mammals prior to ovulation, the surge of luteinizing hormone from the pituitary, normally preceding and initiating ovulation, is effectively blocked. On the other hand, unlike some other reported luteinizing hormone suppressants, the 8-arginine vasotocin does not appear to suppress the basal levels of the hormone in the blood.

It has also been determined that the tripeptide, prolyl-arginyl-glycinamide, i.e. Pro-Arg-Gly(NH$_2$) exhibits a similar luteinizing hormone suppressing effect that also inhibits ovulation. The tripeptide, it will be noted, occurs as the terminal portion of the nonapeptide, 8-arginine vasotocin; however, its free presence as a naturally-occuring substance in the endocrine system is unknown.

At least one other analogue of the tripeptide, i.e. Prolyl-Lysyl-Glycinamide, (wherein Lys = Lysine) also exhibits luteinizing hormone suppressing and anovulatory properties.

The nonapeptide and tripeptides may be administered in all their common pharmacological forms, e.g., as the acetate, hydrochloride, maleate, sulfate and other similar salts. The particular salt form of the peptides does not appear to be important with respect to the exhibited biologic activity. It is only necessary that the salt meet pharmacologic requirements for practical use. In the biological data presented herein below, the peptides were in the acetate-salt form. However, testing of the peptides in the hydrochloride form revealed no significant difference on the luteinizing hormone suppression or anovulatory activity.

The cyclic nonapeptide or the tripeptide suppress LH production when introduced into the mammalian subject at any time prior to time of the expected pre-ovulatory LH surge. The peptide, in the case of the nonapeptide, is introduced by subcutaneous or intravenous or intraperitoneal injection; or in the case of the tripeptide, by injection, or orally. Saline dilutions can be used for injection purposes. Preferably, the peptide introduction takes place prior to the expected LH surge, i.e., at least several hours prior thereto and up to, and including, the generation of the LH surge, if the time of the surge is well established. In the case of the lower mammals, e.g., rodents, these surge times occur with great and well-defined regularity. Therefore, administration of the peptides can be quite precisely determined. In the case of the primates, the LH surge timing is not nearly so well defined, and therefore, peptide may have to be administered over relatively extended periods of time, i.e., several days prior to the expected ovulation. Thus, in the case of the nonapeptide, at least, administration by means of a slow release implant of the peptide may present the most practical method of ensuring the presence of the required peptide levels in the body fluids at the time of the LH surge.

The level of nonapeptide or tripeptide in the body fluids necessary to inhibit the LH surge and subsequent ovulation will vary from species to species and from individual to individual. In this regard, however, the nonapeptide does appear to have at least 50-100 times the activity, on a weight basis, of the tripeptide. Therefore, effective dosage levels of the tripeptides are necessarily higher than the nonapeptides, by as much as two or three orders of magnitude. On the other hand, the tripeptide, being a much simpler molecular, is more easily metabolized, and the higher dosage requirements are easily tolerated and produce no side effects. In fact, no noticable side effects were observed in rats at dosages in the order of several grams/kilograms of body weight, but synthesis techniques from simple amino acids are also available. A technique similar to that disclosed herein for the synthesis of the tripeptide may be utilized; although it will be recognized that the production of a nine membered peptide will be considerably more costly and time consuming that the production of the tripeptide. But such synthesis techniques are available to secure the 8-arginine vasotocin utilized in the present invention.

The following example illustrates a technique for isolating the 8-arginine vasotocin from bovine pineal glands.

EXAMPLE I

Fresh glands (7 lb) were homogenized in a Waring blender and extracted with acetone (12 liters) under constant agitation for 18 hr at 4° C. After filtering, the air-dried solid (310 g) was suspended in water (800 ml) and methanol (400 ml), and the mixture was stirred at 50° for 6 hr, cooled, and centrifuged at 10,000 rpm for 15 min. The supernatant was concentrated at 50° C in vacuo to 700 ml and after cooling to room temperature it was saturated with ammonium sulfate and kept at 4° C for 8 hr. The resultant precipitate (2.5 g) was filtered and dissolved in 0.05 M ammonium hydroxide (50 ml). The solution was extracted with isobutanol (5 × 15 ml), saturated with 0.05 M ammonium hydroxide solution, and after drying the combined extracts with anhydrous magnesium sulfate, the solvent was removed in vacuo.

The residue was dissolved in ammonium acetate solution (0.0r, M, 10 ml), saturated with trichlorbutanol, and applied to a Sephadex G-25 column (4 × 45 cm), prepared in the same buffer. The column was eluted with the buffer at a flow rate of 5 ml/min and the active material was obtained by pooling the fractions between 500 and 580 ml. The pooled fraction was lyophilized and the resultant powder was dissolved in ammonium acetate buffer (pH 7, 0.05 M, 1.0 ml), saturated with trichlorbutanol. The solution was chromatographed on a Bio-Rex 70 column (200-400 mesh., 1 × 40 cm) prepared in the same buffer. The flow rate was adjusted to 4 ml/hr and the active material followed by measuring the fluorescence at 395 mμ of each fraction after addition of phenanthrenequinone. Fractions between 90 and 110 ml contained the nonapeptide, and these were pooled and lyophilized, yielding a white powder (1.4 mg).

Electrophoresis (1200 V, 4 hr) in a pyridine-acetate buffer at pH 3.5 using Whatman 3 MM and detection with hydrochlorous acid/ortho-tolidine gave 3 bands, and the active compound (at 25 cm) was eluted and lyophilized. Descending paper chromatography on Whatman filter paper No. 1, using butanol: acetic acid: water (4:1:5) for 12 hr, and elution of the band at 14.5 cm gave the homogeneous microcrystalline peptide (380 μg).

SYNTHESIS OF THE TRIPEPTIDE

Since the tripeptide does not occur naturally, it must be synthesized. The synthesis of peptides, at least simple ones, such as the tripeptide, has been firmly established in recent years. Any of the well-known techniques may be utilized. By way of illustration, one method may be as follows:

Protected arginine, i.e., tert-butyloxycarbonylnitro-arginine is dissolved in a suitable solvent such as dimethylformamide and tetrahydrofuran. The dissolved protected amino acid is then cooled to a temperature slightly below the freezing point (0° C), whereupon isobutyl chlorocarbonate and triethylamine is added with stirring. After a short period, glycinamide dissolved in dimethylformamide is added. The mixture is then permitted to warm to room temperature and stirred for a period of several hours and then filtered. The filtrate is recovered and evaporated to dryness and then extracted with dimethylformamide. The dimethylformamide solution is precipitated with ethylacetate to yield the dipeptide, i.e., protected arginyl-glycinamide.

The protected dipeptide is then dissolved in concentrated formic acid, left standing for perhaps 15 minutes and then evaporated to dryness, in vacuo. The residue is dissolved in dimethylformamide and the solution is then added to a mixture of protected proline, (carbobenzoxy-proline), triethylamine and isobutyl-carbonate which has been previously stirred at a reduced temperature (−10° C) for some minutes in dimethylformamide and tetrahydrofuran. The entire mixture is then stirred together for several hours at room temperature. The solvent is then removed, in vacuo. The residue is dissolved in dimethylformamide and then precipitated by the addition of ethyl acetate. The solution and precipitation are repeated to thereby yield the protected tripeptide, i.e., carbobenzoxy-prolyl-nitro-arginyl-glycinamide.

The protected tripeptide is dissolved in a mixture of ethanol and acetic acid, and then hydrogenated for some hours (15) with a 10% palladium/charcoal catalyst. The mixture is then filtered and evaporated to dryness, in vacuo, thus yielding the tripeptide product, i.e., the acetate salt of prolyl-arginyl-glycinamide. It will be understood the identical synthesis procedures are utilized to prepare tripeptide analogue, e.g., Pro-Lys-Arg (NH₂).

EXAMPLE II

Utilizing the synthesis technique set forth above, 3.04 grams of tert-butyloxycarbonylnitro-arginine was reacted with 0.74 grams of glycinamide to yield 2.8 grams of carbobenzoxy-proline to yield 3.2 grams of the protected tripeptide, carbobenzoxy-prolyl-nitro-arginyl-glycinamide. One half gram of the protected tripeptide yielded 0.36 grams of the tripeptide acetate product after hydrogenation.

BIOLOGICAL ACTIVITIES

The biological activities of the cyclic nonapeptide, 8-arginine vasotocin, and the tripeptide, prolyl-arginyl-glycinamide, and at least one analogue of the tripeptide, namely, prolyl-lysyl-glycinamide, have been investigated. In order to elucidate the peptides abilities to influence the pre-ovulatory surge of LH from the pituitary and the release of ova from the ovaries, experiments were conducted with female rats. p In these studies, rats that positively exhibited regular estrus cycles, were selected. These subjects were administered various dosages of the peptides of the invention as well as control materials, i.e., saline solution alone, and the naturally occuring peptides, vasopressin and oxytocin, that are related to the cyclic nonapeptide, 8-arginine vasotocin. Both vasopressin and oxytocin are well documented in the literature. Vasopressin is very closely related to 8-arginine vastocin, and has the cyclic nonapeptide structure:

Cys-Tyr-Phe-Glu(NH₂)-Asp(NH₂)-Cys-Pro-Arg-Gly(NH₂)

wherein the 3rd amino acid moiety is phenylalanine rather than isoleucine that occurs in the 8-arginine vasotocin. In all other respects the vasopressin peptide chain is identical to 8-arginine vasotocin. Vasopressin is found in the posterior lobe of the pituitary gland.

Oxytocin, like vasopressin, is a peptide hormone also found in the posterior pituitary gland. It is also a cyclic nonapeptide and has the formula:

Cys-Tyr-Ileu-Glu(NH₂)-Asp(NH₂)-Cys-Pro-Leu-Gly(NH₂).

Both vasopressin and oxytocin exhibit biological (hormonal) effects upon the mammal. Vasopressin regulates and mediates the secretion of water from the body; while oxytocin is principally responsible for uterine contraction during parturition, and lactation stimulation. It should be noted that both hormones are closely related to 8-arginine vasotocin, whereby their effect upon the pre-ovulatory LH surge and ovulation is of interest.

More specifically, in normal cycling female rats there is a dramatic surge in the level of luteinizing hormone (LH) in the blood on the afternoon of proestrus. This surge of LH can be detected by monitoring periodic blood samples. These samples are secured by inserting a cannula into the right atrium of the heart. 50 microliters of blood are withdrawn each hour for some 6 to 7 samples. The levels of LH therein is determined using radioimmunossay techniques. Under normal circumstances, ovulation occurs about 12 hours later. The oviducts are then removed and the ova are recovered therefrom by inserting a hypodermic into the tubal ostium and flushing with phosphate-buffered saline. Freed ova are collected in a micropipette and counted. In the tests, the normal cycling rats were administered both control saline, and various dosages of 8-arginine vasotocin, prolyl-arginyl-glycinamide, prolyl-lysyl-glycinamide, vasopressin and oxytocin.

Table I presented below presents the results of tests comparing the LH and ovulation inhibitory effects of the indicated peptides.

TABLE I

Effect in proestrus rats of tripeptides and cyclic nonapeptides on the preovulatory surge of LH and ovulation.

| Compound | Dosage | Number of Animals | Presence of LH Surges (%) | Presence of Ova (%) |
|---|---|---|---|---|
| Saline | | 56 | 98 | 96 |
| 8-arginine-Vasotocin | 1.0 μg | 32 | 5 | 22 |
| | 0.1 μg | 18 | 34 | 45 |
| Vasopressin | 1.0 μg | 29 | 37 | 62 |
| | 0.1 μg | 18 | 94 | 94 |
| Oxytocin | 5.0 μg | 16 | 94 | 94 |
| | 1.0 μg | 20 | 100 | 100 |
| Prolyl-arginyl-glycinamide | 0.6 mg | 12 | 25 | 42 |
| Prolyl-lysyl-glycinamide | 0.6 mg | 13 | 15 | 30 |

In every instance, the peptide dosage was administered in saline via heart cannula at one hour intervals over a 4 hour period.

The data indicates that ocytocin is essentially inactive, having an LH an ovulation inhibitory effect, essentially no better than plain saline itself. Vasopressin does exhibit considerable activity, but much less than 8-arginine vasotocin at the same dosage levels. Vasopressin is unsuitable for use in the method of the invention due to its severe vasocontrictive side effects. Both the tripeptides, prolyl-arginyl-glycinamide, and its analogue, prolyl-lysyl-glycinamide, also exhibit high inhibition of the LH surge and ovulation, although not quite so high as 8-arginine vasotocin or vasopressin. In addition, there is positive indication that the cyclic nonapeptides of the invention inhibit the prolactin surge that is a normal characteristic of the mammalian ovulatory cycle. 8-arginine vasotocin, vasopressin, and oxytocin were administered at various dosage levels and rates to a number of rats. Saline solution was utilized as a control. Table II below sets forth the dosage regimen and the results:

TABLE II

Effect on Pre-Ovulatory Surge of Prolactin

| Compound | Dosage | Total Dose | Number of Animals | Presence of Prolactin Surge (%) |
|---|---|---|---|---|
| Saline | — | — | 29 | 93 |
| 8-arginine-Vasotocin | 1μ/30 min | 7 μg | 23 | 4 |
| | 1μ/60 min | 4 μg | 7 | 14 |
| " | 1μg/120 min | 2 μg | 6 | 0 |
| " | 1μg/240 min | 5 μg | 5 | 80 |
| Vasopressin | 1μg/30 min | 7 μg | 6 | 17 |
| " | 1μg/120 min | 2 μg | 7 | 57 |
| Oxytocin | 1μg/30 min | 7 μg | 5 | 60 |
| " | 1μg/120 min | 2 μg | 6 | 84 |

The results agree with the data set forth in Table I, i.e., 8-arginine vasotocin exhibits a high inhibitory effect, vasopressin a lesser effect, and oxytocin the lowest effect.

In the above data, the peptides were administered in the acetate salt form. To illustrate the fact that other salt forms of the peptides do not affect the activity, some 8-arginine vasotocin was recovered from methanolic hydrochloric acid, to yield the dihydrochloride form. One microgram dosages of the dihydrochloride were administered to ten rats under the same conditions as noted in Table I. The results are shown in Table III.

TABLE III

| Compound | Dosage | Number of Animals | Presence of LH Surges (%) | Presence of Ova (%) |
|---|---|---|---|---|
| 8-arginine vasotocin-dihydrochloride | 1 μg | 10 | 0 | 20 |

Thus, it is apparent that the introduction of either 8-arginine vasotocin into a mammal in higher levels than normally found within the body, will inhibit the pre-ovulatory LH surge and produce an anovulatory effect. Similarly the tripeptide, prolyl-arginyl-glycinamide, and the analogue tripeptide, prolyl-lysyl-glycinamide exhibit the same biological activities. The introduction of these peptides into the mammalian body presents a method for control of fertility and an alternative to other methods currently practiced.

It should also be understood that spermatogenesis in the mammalian male is also dependent upon the secretion of gonadotropins from the pituitary. In addition, LH is directly responsible for androgen production which in turn is necessary for maturation of sperm and maintenance of the reproduction tract. To the extent the cyclic nonapeptides and tripeptides of the invention interfere with LH secretion, it is apparent that spermatogenesis can be reduced or eliminated by administering the peptides to a male subject. Since spermatogenesis is a continual process which does not involve a dramatic surge of LH, it is clear that continued low levels of the peptides must be maintained in the subject to effectively inhibit production. Slow-release long-acting implants of the peptides are therefore indicated as a suitable method of reducing male fertility.

What is claimed is:

1. A method for reducing fertility in female mammals by suppressing the pre-ovulatory surge of luteinizing hormone with resultant inhibition of ovulation and fertility, comprising introducing into the mammal during the pre-ovulatory period an effective amount of a cyclic nonapeptide having the formula:

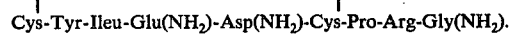

Cys-Tyr-Ileu-Glu(NH$_2$)-Asp(NH$_2$)-Cys-Pro-Arg-Gly(NH$_2$).

2. The method of claim 1 wherein the cyclic nonapeptide is introduced into the mammal in a total dose of from about 0.5 to about 5 micrograms per kilogram of body weight.

3. The method of claim 1 wherein the cyclic nonapeptide is a pharmacologically acceptable salt thereof.

4. The method of claim 2 wherein the cyclic nonapeptide is in the acetate salt form.

5. The method of claim 2 wherein the cyclic nonapeptide is in the hydrochloride salt form.

6. A method for reducing fertility in a female mammal by suppressing the pre-ovulatory surge of luteinizing hormone with resultant inhibition of ovulation and fertility, comprising introducing into the mammal during the pre-ovulatory period an effective amount of a tripeptide having the formula:

Pro-Arg-Gly(NH$_2$).

7. The method of claim 6 wherein the tripeptide is introduced into the mammal in a total dose of from about 5 micrograms to about 5 milligrams per kilogram of body weight.

8. The method of claim 5 wherein the tripeptide is a pharmacologically acceptable salt thereof.

9. The method of claim 6 wherein the tripeptide is in the hydrochloride salt form.

10. As a composition of matter the tripeptide, Pro-Arg-Gly($NH_2$).

11. A method for reducing fertility in a mammal by reducing the proestrus surge of luteinizing hormone and the number of ova released during estrus, comprising introducing into the mammal during the proestrus period an effective amount of a tripeptide having the formula:

Pro-Lys-Gly ($NH_2$).

12. As a composition of matter, the tripeptide, Pro-Lys-Gly($NH_2$).

13. Pharmacologically acceptable salts of the tripeptide of claim 10.

14. Pharmacologically acceptable salts of the tripeptide of claim 12.

15. A method for reducing fertility in male mammals by reducing the secretion of luteinizing hormone from the pituitary, comprising introducing into the mammal over an extended period an effective amount of the cyclic nonapeptide, 8-arginine vasotocin.

16. The method of claim 15 wherein the tripeptide, prolyl-arginyl-glycinamide, is substituted for the cyclic nonapeptide.

17. The method of claim 15 wherein the tripeptide, prolyl-lysyl-glycinamide, is substituted for the cyclic nonapeptide.

* * * * *

UNITED STATES PATENT OFFICE
CERTIFICATE OF CORRECTION

Patent No. 4,081,533          Dated  March 28, 1978

Inventor(s) Dr. Dean W. Cheesman

It is certified that error appears in the above-identified patent and that said Letters Patent are hereby corrected as shown below:

Column 1, line 17 change "gonodotropins" to
                        --gonadotropins--

Column 2, line 12, change "inibiting" to --inhibiting--

Column 6, line 12, remove the "p" after "rats."

Column 6, line 22, change "vastocin" to --vasotocin--

Signed and Sealed this

Twenty-sixth Day of September 1978

[SEAL]

Attest:

RUTH C. MASON
*Attesting Officer*

DONALD W. BANNER
*Commissioner of Patents and Trademarks*